US008541065B2

(12) United States Patent
Lukowski et al.

(10) Patent No.: US 8,541,065 B2
(45) Date of Patent: Sep. 24, 2013

(54) METHOD FOR COATING SURFACES WITH MICROPARTICLES AND NANOPARTICLES WITH THE AID OF PLASMA METHODS

(75) Inventors: Gerold Lukowski, Greifswald (DE);
Karsten Schroeder, Greifswald (DE);
Wolf-Dieter Juelich, Greifswald (DE);
Ruediger Foest, Neuenkirchen (DE);
Klaus-Dieter Weltmann, Binz (DE);
Joerg Ehlbeck, Hinrichshagen (DE)

(73) Assignee: INP Greifswald, Leibniz-Institut fuer Plasmaforschung und Technologie e.V., Greifswald (DE)

( * ) Notice: Subject to any disclaimer, the term of this patent is extended or adjusted under 35 U.S.C. 154(b) by 583 days.

(21) Appl. No.: 12/602,331

(22) PCT Filed: May 31, 2008

(86) PCT No.: PCT/EP2008/056730
§ 371 (c)(1),
(2), (4) Date: Jun. 7, 2010

(87) PCT Pub. No.: WO2008/145750
PCT Pub. Date: Dec. 4, 2008

(65) Prior Publication Data
US 2011/0159273 A1 Jun. 30, 2011

(30) Foreign Application Priority Data

May 31, 2007  (DE) .................. 10 2007 025 452
Dec. 18, 2007 (DE) .................. 10 2007 061 624

(51) Int. Cl.
*H05H 1/00* (2006.01)
*B05D 3/00* (2006.01)
*B05D 1/12* (2006.01)

(52) U.S. Cl.
USPC ............................ 427/536; 427/2.1; 427/180

(58) Field of Classification Search
USPC ................. 427/532, 533, 535, 536, 569, 575, 427/2.1, 180, 189, 331, 2.24, 2.25, 2.28
See application file for complete search history.

(56) References Cited

U.S. PATENT DOCUMENTS

| 2007/0087131 A1 | 4/2007 | Hutchinson et al. |
| 2008/0075731 A1 | 3/2008 | Mohapatra et al. |
| 2008/0081130 A1* | 4/2008 | Farnia et al. ................. 427/577 |
| 2008/0118734 A1* | 5/2008 | Goodwin et al. ............ 428/221 |

FOREIGN PATENT DOCUMENTS

| DE | 10 2005 013 857 | 9/2006 |
| DE | 10 2005 020 168 | 11/2006 |
| JP | 2007 182605 | 7/2007 |
| WO | 2007 127480 | 11/2007 |
| WO | 2008 068154 | 6/2008 |

* cited by examiner

*Primary Examiner* — Dah-Wei Yuan
*Assistant Examiner* — Nga Leung V Law
(74) *Attorney, Agent, or Firm* — Oblon, Spivak, McClelland, Maier & Neustadt, L.L.P.

(57) ABSTRACT

The invention relates to a method for coating surfaces with micro- and nanoparticles, the micro- and nanoparticles being chemically bonded to the surface, comprising the steps of pre-treatment of the surface with a plasma method, simultaneous or subsequent application of the micro- and nanoparticles to the surface, and subsequent fixation of the micro and nanoparticles on the surface using a plasma method, characterized in that the fixation of the micro- and nanoparticles takes place with the aid of anisothermal plasmas, the median electrical energy of which lies in the range of the bond dissociation energy of the micro- and nanoparticles, thus allowing the strength of the chemical bond between the surface and the micro- and nanoparticles to be variably set.

8 Claims, 9 Drawing Sheets

METHOD FOR COATING SURFACES WITH MICROPARTICLES AND NANOPARTICLES WITH THE AID OF PLASMA METHODS

The invention relates to disinfection of surfaces, to deposition of layers that contain microparticles and nanoparticles, and to their immobilization with the aid of plasma methods. Possible areas of application are medical products, surfaces of service devices that come into contact with bacterial contaminants, as well as products used pharmaceutically.

SPECIFICATION

Medical products and instruments must be used in sterile manner in certain applications, because of their intended use. The term "sterile" combines freedom from biological entities with the ability that these reproduce, such as microorganisms (bacteria and fungi) or transfer genetic material, for example phages, viruses, plasmids, prions, or infectious nucleic acids (K. H. Wallhäusser, Georg Thieme Verlag, Stuttgart, New York, 1995).

When used as intended, medical products and instruments are contaminated and colonized with microorganisms. It is advantageous if freedom from germs or at least a paucity of germs on the surface can be maintained for an extended period of time, even during intended use. The advantage of a paucity of germs is particularly great on the surface of implants. The infection rate for permanent implants mainly lies between 0.5 and 6% [Kohnen & Jansen, 2001]. Prevention strategies are urgently necessary.

Another example is infections on catheters. Together with candida, staphylococci are the most frequent pathogens in catheter-associated sepsis, about 50% of which are fatal. In Germany, 3000 to 4000 catheter-associated deaths are assumed to occur per year.

It is the aim of the invention according to the patent to clearly make the adhesion of microorganisms to the surface of medical products or instruments more difficult or actually to prevent it. In the case of medical products for which conditioning for re-use is planned, a paucity of germs leads to a clearly lesser burden of pyrogens.

STATE OF THE ART

In the present invention, plasma-supported disinfection of medical products and instruments is combined with modification of surfaces by means of nanotechnology.

For this reason, the state of the art will be briefly presented in the following, for both work steps.

1. Plasma-Supported Disinfection

For sterilization of medical devices and materials, there are established methods such as sterilization with moist heat, sterilization with gas (ethylene oxide, formaldehyde), sterilization with high-energy radiation. Each of these sterilization methods, however, has specific defects. For example, in treatment with ethylene oxide or formaldehyde, toxic residues of the active substance occur. Sterilization with gamma rays is only possible with special shielding and frequently causes irreversible material degeneration (for example the occurrence of brittleness). In the case of thermally unstable materials, on the other hand, heat or steam sterilization is not possible at all. An alternative method that circumvents the aforementioned disadvantages is plasma sterilization. The interaction of gas discharge plasmas with biological material, particularly the germ-reducing effect, has been the object of many different studies (see, for example, Laroussi et al., New J. Phys., 5 (2003), 41.4, Moreau et al., J. Appl. Phys., 88, 2 (2000), 1166, or Awakowicz and Keil, VFPREO, 5 (2001), 294).

At present, the following patent literature already exists within this subject area:
  with regard to method peculiarities of plasma sterilization (Fraser et al., U.S. Pat. No. 3,948,601 A, 1973; Jacob, U.S. Pat. No. 5,087,418 A, 1990; Martens & Caputo, U.S. Pat. No. 5,482,684 A, 1994; Monroe, U.S. Pat. No. 5,163,458 A, 1991; Spencer & Addy, U.S. Pat. No. 5,656,238 A, 1994), with regard to removing endotoxins by means of plasma sterilization (Banks et al., U.S. Pat. No. 6,558,621 B1, 2000),
  with regard to the combination of plasmas and antibacterial coatings/fluids in the sterilization of surfaces (Caputo et al., U.S. Pat. No. 6,261,518 B1, 1998), and
  with regard to surface sterilization of medical products (for example Moulton et al., DE 69126312 T, 1991; Pickel, DE 101 34 037 A1, 2001).

The latter are concerned with the sterilizing effect of low-pressure plasmas on plastics (PE, PET, UHMWPE, PLL) and metal substrates (titanium, steel). Studies have shown that sufficient germ reduction can be achieved with these methods. Cross-linking or formation of brittleness of the UHMWPE materials occurred only to a slight degree.

The STERRAD sterilization system of the Johnson & Johnson company (see U.S. Pat. No. 5,785,934 A and M. Fortsch et al., Ophthalmologe {Ophthalmologist} 90, 1993, No. 6, p. 754-764), which work under low-pressure conditions, has achieved the greatest dissemination up to now as a method for plasma sterilization of thermally unstable medical instruments that is gentle on the material. The long treatment times that are necessary in the STERRAD method are attributable, on the one hand, to the short lifetime of the reactive species and the related low decomposition rates of organic material, and, on the other hand, to problems with fully exposing germs in the event of clumping and irregular or cracked surfaces. A significant disadvantage consists in the choice of hydrogen peroxide as the gas. Hydrogen peroxide vapor is strongly absorbed by materials that contain cellulose. For this reason, this plasma sterilization cannot be used for sterilization material that contains cellulose. All packaging materials must be free of cellulose and are only available from the operator company. Instrument containers, such as those already available for steam sterilization, are only now being developed for plasma sterilization. The instruments must be completely dry before charging the sterilizer. In the event of organic contamination of the surface, the effect of plasma sterilization is significantly restricted. The product was approved for marketing by the Food and Drug Administration (FDA) in the United States. The Abtox Plazlyte Sterilization System was developed as a competitive product; in contrast to the Sterrad system, it uses peracetic acid. In 1998, these devices were recalled by the FDA.

Aside from low-pressure plasma methods, the use of anisothermal plasma methods based on normal pressure was proposed for sterilization. A number of excitation methods can serve to generate these plasmas, including corona discharge, dielectrically impeded discharge, capillary discharge, and microwave discharge. Excitation takes place by way of an electric field, which acts in continuous or pulsed manner and comprises the frequency range from 0 (DC) to a few GHz. An essential prerequisite for achieving an effective germ-killing effect in the treatment of surfaces is that uniformity of the action mechanisms be maintained over the entire substrate to be treated. Technical solutions here include a guided gas stream that first passes by the active plasma zone before the reactive species formed in the plasma pass over the region to be decontaminated ("downstream"). Technical solutions of this type have been proposed for a beam plasma, for example in the U.S. Pat. No. 6,194,036 B1 (see H. W. Herrmann et al., Physics of Plasmas, Vol. 6, No. 5, 1999, p. 2284-2289) and described for decontamination in the interior of containers, partly with the admixture of alcohol into the carrier gas (Crowe, R. et al., WO 03/063914 A2, 2002).

The following references also belong to the prior art: EP 0981 381 B1=DE 698 37 141 T2; DE 102005044360 A1; DE 102005013857 A1, and DE 10102465 A1. EP 0981 381 B1 is aimed in general at polyhydroxyalkanoate polymers and production methods for removing endotoxins and their use in different biomedical applications, including tissue engineering, wound bandages, administration of medications, and in prostheses. The polyhydroxyalkanoates are also modified in the annexed side chains, among other things with a gas plasma. Nanoparticles and/or microparticles made from latex are also described, but not in connection with a plasma. EP 0981 381 B1 describes the functionalization of organic materials for biomedical applications. A variant is the treatment of surfaces with a cold plasma. This can be used, for example, for cleaning purposes, to increase cell adhesion, or for sterilization (paragraphs 49, 50, 52). However, no relationship between plasma coating and microparticles and nanoparticles is shown in EP 0981 381 B1.

DE 102005044360 A1 relates to a medical technology product equipped with an antimicrobial agent made from a complex material of metal nanoparticles and macromolecules, whereby the macromolecules are at least partly formed from a polyamino acid. Plasma activation is also mentioned, but not in combination with the nanoparticles.

From DE 102005013857 A1, a method for the production of antibacterial surfaces is known, in which nanoparticles are applied and a plasma pretreatment of the surface to be coated takes place before it is coated (claim 1; paragraph 41, paragraph 44). However, fixation of the particles by means of a plasma is not mentioned there.

DE 10102465 A1 describes a method for the production of amphiphilic polymers that can also be used as coating agents (paragraph 3). With the aid of the method, it is also possible to produce nanoparticles that are based on liposomes and can be functionalized (paragraphs 11, 12). However, chemical bonding of nanoparticles to a surface is not described.

2. Use of Nanotechnology for Modification of Surfaces

Various materials are used for coating medical products:
silver nanoparticles,
titanium dioxide nanoparticles for the production of photocatalytic surfaces,
diamond coatings,
hydroxylapatite nanoparticles,
metal/ceramic coatings and ceramics,
organic nanofibers and composite materials,
nanostructured aluminum oxide surfaces.

2.1 Surfaces with Silver Nanoparticles

At present, silver is increasingly stepping into the focus of research, because of the increase in antibiotic-resistant germs and the development of new application forms. Since silver acts on various cell structures of gram-positive and gram-negative bacteria, the development of resistances is unlikely. Particularly small particles are advantageous for processing silver in metallic form. Their large surface area ensures sufficient and uniform release of silver ions even in the case of small amounts of silver, in order to achieve an antiseptic effect. There are numerous examples for the use of nanoparticulate silver.

Silver nanoparticles are mixed into polymers and surface coatings, for example, which are already used or will be used in medicine, for articles of household hygiene and care (Hanke & Guggenbichler, U.S. Pat. No. 6,720,006 B1,2001), as well as for hygiene in public facilities. Such silver particles are already commercially available (Bio-Gate GmbH). In medicine, nanoparticles are worked into polymers for catheters and implants, in microfine distribution, or applied to instruments as a thin coating (for example Sicuris silver catheter, Siemens AG). Studies have documented a significant reduction in infection rates from the use of catheters having a silver content. Furthermore, contact lenses were developed that contain nanoparticulate silver, among other things (Vanderlaan et al., EP 1 355 681 A1, 2001). An adhesive with a nanosilver content is available for connecting components in medical technology.

The antiseptic properties of silver are also used to avoid or combat infections of acute or chronic wounds. For this purpose, the silver is combined with materials that serve to manage the wound exudate (for example with activated charcoal, hydropolymers, or hydrocolloids). Nanocrystalline silver is used in the wound dressing Acticoat (Smith & Nephew).

Another approach for the use of nanosilver consists in the development of antiseptic paints for interior rooms, which can be used in clinics, for example. Furthermore, paints that are water-soluble or low in solvents, are easy to apply, and contain nanosilver are offered for sale for treatment of medical devices and consumables, as well as for use in prosthetics (Sarastro GmbH).

Textiles are also equipped with silver particles (Padycare®, Tex-a-med GmbH). Efforts are being made to produce work clothing from these fibers, for example, particularly for the medical sector.

A significant disadvantage of silver, particularly when it is used in combination with nitrate or sulfadiazine, consists in that it can trigger side effects such as allergies or an inhibition of wound healing during treatment.

2.2 Titanium Dioxide in Photocatalytic Surfaces

Titanium dioxide is the material most frequently used as a photocatalyst. The electrons of titanium dioxide can be excited with energy from daylight or artificial light. This process leads to the formation of highly reactive radicals that destroy microorganisms and chemical substances situated on the surface of the particles. The titanium dioxide particles used for the production of photocatalytic surfaces possess a diameter of less than 100 nm, since nanoscale particles demonstrate a greater photocatalytic effect and are transparent (Sherman, U.S. Pat. No. 6,653,356 B1, 2000; Yadav et al., U.S. Pat. No. 6,572,672 B1, 2002).

In order to be able to provide surfaces of the most varied materials with photocatalytic coatings, corresponding paints were developed (Akarsu, DE 102 35 802 A1, 2002; Beling & Mehner, DE 199 62 055 A1, 1999).

Photocatalytic surfaces can also be modified in such a manner that they additionally release metal ions that have an antibacterial effect, such as copper or silver ions. In Japan, photocatalytic products are already being marketed and used to reduce the germ count in operating rooms, for example.

2.3 Nanostructured Surfaces of Implants

In order to lengthen the useful lifetime of joint implants, materials that have a greater wear resistance are being sought, which can also be processed well and are characterized by a low risk of fracture. One solution approach consists in the use of nanostructured surface coatings. These lead to a reduction in wear, on the one hand, and on the other hand make structures available that promote the growth of cells and thus the healing process. For example, it was possible to show that the adhesion of osteoblasts on nanostructured $TiO_2$ surfaces is clearly stronger than on conventional $TiO_2$ surfaces. An overview concerning the production of coatings, the materials used, and the requirements for the surfaces is given by Thull, R., Biomolecular Engineering 19, 43-50 (2002), Enzyklopädie Naturwissenschaft and Technik {Encyclopedia of Natural Sciences and Technology}, $8^{th}$ supplemental volume, 1-7 (2003).

Stents are also coated with titanium materials. The surfaces produced in this connection, which cannot be wetted easily, improve blood compatibility, reduce the growth of cells on the implant surface, and lower the risk of the formation of blood clots (Biehl et al., J. Biomed. Mater. Res., 2002; Eisenbarth et al., Biomol. Eng. 19, 233-237 (2002)).

Diamond Coatings

To improve the wear behavior of implants, protective coatings made from diamond are being developed (Goldstein et al., 1996, U.S. Pat. No. 6,709,463 B1, 2000; Riiffer et al., 2003). The diamond layers are applied with the aid of the CVD method. In comparison with conventional diamond coatings, they demonstrate very small surface structures of only approximately 15 nm, are hard and impact-resistant, and are characterized by a low friction coefficient. In laboratory and animal experiments, a high level of biocompatibility and biotolerance of the diamond surface was shown. For example, they could not be attacked by bodily fluids and did not provoke any allergic or pathomorphological reactions. Nanocoatings made from diamond are credited with the ability to increase the useful lifetime of cobalt/chrome and titanium implants to more than 40 years (Catledge et al., J. Nanoscience and Nanotechnology 2 (3-4), 293-312, 2002).

Hydroxylapatite

Because of its low strength, hydroxylapatite is not suitable as a support material for implants that are subject to stress. However, it is used to coat titanium and cobalt/chrome implants. The nanostructured surfaces demonstrate structural properties that are very similar to those of apatite in bone and dentine. This improves the cell adhesion as well as proliferation and mineralization of the surrounding tissue (Catledge et al., Nanoscience and Nanotechnology 2 (3-4), 293-312 (2002)).

For medical applications, hydroxylapatite is applied, in most cases, with the aid of the plasma spray method. The grain size of the coating then lies at 15-25 nm. Smaller grain sizes cannot be achieved with this method, since a finer starting material would completely evaporate at the high temperature. This is a decisive disadvantage, since the grain size is a determining factor for the adhesion behavior of the hydroxylapatite coating on the surface. For this reason, new types of coating methods such as ion beam sputtering and pulsed laser deposition are being investigated at this time. Preliminary results have shown that the surfaces produced using these methods demonstrate improved properties with regard to durability and friction wear resistance. Furthermore, the material releases small amounts of calcium and phosphate ions, which stimulate bone growth.

Additionally, it should be pointed out that nanocrystals of hydroxylapatite and tricalcium phosphate, which is chemically closely related to it, are also very well suited as bone replacement materials (VITOSS®, Orthovita; Ostim®, Osartis GmbH & Co. KG; Roessler, U.S. Pat. No. 6,706,273 B1, 2001). The great porosity of these products allows rapid ingrowth of blood vessels and bones. The materials can be introduced into defects with shape fit, and can be decomposed by the organism, to a great extent, within a period of a few months.

Metal/Ceramic Coatings and Ceramics

Wear of the joint socket can have the effect of limiting the useful lifetime of joint implants. To reduce friction wear, joint heads were provided with ceramic surfaces. Since ceramics do not adhere well to metal surfaces, nanocrystalline Cr—Ti—N coatings were developed. These possess a metallic character on their inside, on the joint head, which imparts a good bond to the carrier material and decreases towards the outside. Preliminary experiments have shown that in this manner, wear of the joint socket is greatly reduced. The suitability of the material for in vivo use is still being investigated. The implant material itself can also have a nanostructured ceramic surface. This is produced in a sintering process, from $TiO_2$ and $Al_2O_3$ nanopowders, or using the sol/gel process and subsequent sintering. Nanostructured ceramic surfaces are characterized by a high level of biocompatibility and represent a suitable growth substrate for osteoblasts at suitable grain sizes.

Organic Nanofibers and Composite Materials

Carbon nanofibers have extraordinary mechanical properties such as an advantageous ratio of tear resistance and weight, for example, as well as a nanoscale geometry that is similar to that of crystalline hydroxylapatite in bone. PCU carbon nanofibers increase the cell adhesion of osteoblasts, for example. This was also demonstrated for nanostructured PLGA titanium composite, the surface and chemical properties of which might be strongly similar to those of bone (Kay et al., Tissue engineering, 8, 753-761, 2002).

2.4 Nanoporous Surfaces

Nanoporous surfaces are produced on stents, among other things. Thus, an aluminum layer was applied to the stent, with the aid of a newly developed plasma method, which layer was subsequently converted to nanoporous, amorphous aluminum oxide, in a wet chemical process. By means of embedding radioactive nuclides into the pores of the aluminum coating, whose diameters can be varied between 10 and 100 nm, controlled release of radioactivity can be achieved, and thus the risk of renewed vascular occlusion can be reduced.

The principles that underlie the nanoporous surfaces of the stents were transferred to seeds. These are very small rods that also have a nanoporous surface. In the case of seeds, as well, the surface serves as a carrier for radioactive nuclides. For protection against the release of nuclides, the small rods are encapsulated in titanium, whereby the radiochemical yield reaches almost 100%. Seeds can be used as implants for local radiation therapies, such as in the case of prostate carcinoma, for example.

Aluminum oxide membranes were also used in drug delivery systems as nanoporous surfaces (Brandau et al., U.S. Pat. No. 6,709,379 B1, 2001). It was possible to produce pore diameters in the nanometer range. These membranes possess all the advantages of inorganic materials with regard to their temperature resistance and the resistance to acids, bases, or solvents, for example. Since the pore diameter can be freely selected between approximately 10 and 100 nm, membranes with different oxygen exit kinetics can be produced.

2.5 Lipid Nanoparticles

There are no studies concerning coating medical products with lipid nanoparticles, according to our searches. Previous patents relate to the encapsulation of active substances in lipid nanoparticles and their use in cosmetics, as drug delivery systems (Müller & Olbrich, DE 199 64 085 A1, 1999) or for UV protection (Heppner et al., DE 199 52 410 A1, 1999; Müller et al., DE 100 16 155 A1, 2000). Mantling of lipid nanoparticles was also developed (Burger et al., DE 10210449 A1, 2002).

The searches furthermore showed that the combination of plasma sterilization or plasma disinfection and lipid nanoparticles and their special properties were not described until now. Therefore, to our knowledge, there is no prior art to counter the invention described below.

3. Combination of Sterilization and Coating

In all the methods known until now, coating of the surface takes place first, followed by germ reduction (disinfection) or sterilization as the final work step. In the case of coating using sensitive materials, the surface structure that is achieved is partly destroyed by the energy introduced during sterilization.

TASK OF THE INVENTION

Proceeding from the state of the art, the invention was based on the task of eliminating the disadvantages of the different solutions as indicated above, and of making available new, improved possibilities for coating surfaces as well as for germ reduction and/or sterilization.

DESCRIPTION OF THE INVENTION

Figure 1:
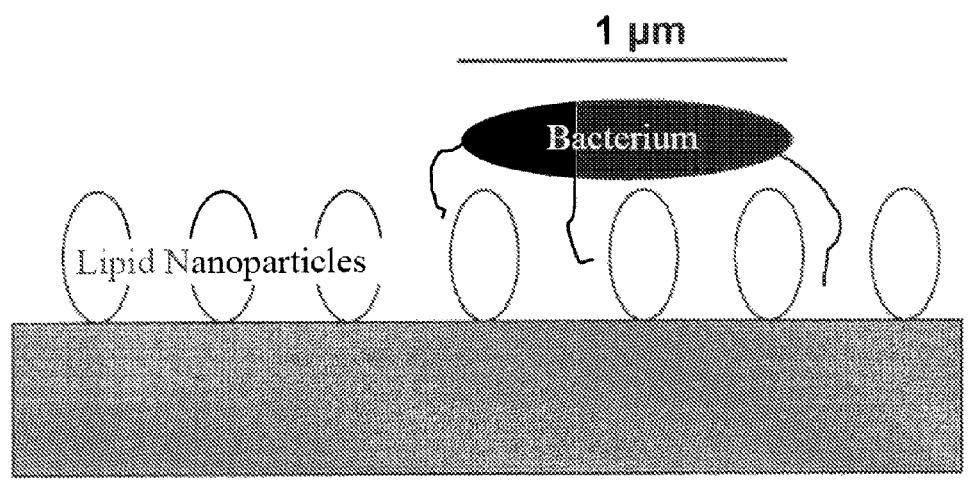
FIG. 1 shows lipid nanoparticles on a surface at intervals less than the size of a bacterium.

The task was accomplished in accordance with the characteristics of the claims. According to the invention, it was made possible to develop a new method for coating medical products with nanoparticles and microparticles, by means of which method germ contamination is prevented or made more difficult, when used as intended. The method was developed in such a manner that disinfection and coating are carried out either at the same time, or in multiple work steps that follow one another.

The method according to the invention for coating surfaces with microparticles and nanoparticles, wherein the microparticles and nanoparticles are chemically bonded to the surface, consists of the following steps:
pretreatment of the surface using a plasma method, to implement defined structures,
simultaneous or subsequent application of the microparticles and nanoparticles to the surface,
subsequent fixation of the microparticles and nanoparticles on the surface by means of a plasma method,
characterized in that the fixation of the microparticles and nanoparticles takes place with the aid of anisothermal plasmas, whose average electron energy lies in the range of the bond dissociation energy of the microparticles and nanoparticles, and thereby the strength of the chemical bond between the surface and the microparticles and nanoparticles can be adjusted in variable manner.

The term "chemical bond" means that either a covalent bond, a hydrogen bridge bond, or a van der Waals bond between the particles and the surface is produced.

Anisothermal (synonym: non-thermal or non-equilibrium) plasmas represent a class of plasma far from thermodynamic equilibrium. In particular, the average kinetic energies of different plasma components in anisothermal plasmas deviate from one another. Here, electrons reach an average kinetic energy in the range of several eV, while that of the ions and neutral particles generally lies up to several orders of magnitude below this. On the other hand, there are thermal plasmas that are in thermodynamic equilibrium, in other words their components (electrons, ions, and neutral particles) possess a Maxwell velocity distribution, and therefore these plasmas are characterized by a (single) temperature. (Example: local regions of arc discharge, plasma welding).

The bond dissociation energy, in chemistry, means the amount of energy required to split an atom bond completely into two radicals. It is a measure of the strength of an atom bond and is therefore also frequently referred to as bond energy or bond enthalpy. For example, the bond dissociation energy of lipids lies in the range of 2-6 eV.

Because of the fact that the average electron energy lies in the range of the bond dissociation energy of the microparticles and nanoparticles, and thus the strength of the chemical bond between the surface and the microparticles and nanoparticles can be adjusted in variable manner, the result was achieved, for the first time, that surfaces are now obtained on which the microparticles and nanoparticles applied retain their functionality completely. Furthermore, the result is achieved that for reconditioning of the surfaces, the microparticles and nanoparticles applied can be easily (more or less) removed. This is very advantageous particularly in the case of medical devices.

The object of the invention is also a method that is characterized in that lipids having a low melting point are selected for the coatings, so that the coatings are stable at body temperature, but are removed again in a chemical disinfection washing method between 50-80° C. The method according to the invention, for the production of a coating of a surface with microparticles and nanoparticles that is stable at body temperature, which can be removed again with a chemical disinfection washing method between 50-80° C., is characterized in that lipids having a low melting point are selected, which are fixed in place on the material surface, preferably by means of a dipping method, after conversion to microparticles and nanoparticles, preferably by means of high-pressure homogenization.

The pretreatment of the surface and/or the fixation of the microparticles and nanoparticles on the surface preferably take place using a non-thermal plasma method. By means of targeted plasma pretreatment, preferably at a water contact angle of less than 50°, it is possible to disinfect surfaces and, at the same time, to improve the hydrophilia in such a manner that nanoparticles and microparticles that contain lipids, for example, are distributed particularly well on the surface. Application of nanoparticles and/or microparticles shortly afterwards or subsequently prevents the surface from becoming recontaminated with microbial growth, as well as contamination of the surface due to contact with organic material, such as blood components, for example. The nanoparticles and microparticles that are applied according to the invention are characterized by particular physical/chemical properties. During the subsequent fixation of the microparticles and nanoparticles using the plasma method, covalent bonds and/or hydrogen bridge bonds or van der Waals bonds of the particles are formed.

The average electron energy for fixation of the microparticles and nanoparticles lies in the range of 0.01 to 10 eV, preferably in the range of 0.5 to 5 eV. The average electron energy of the plasma for pretreatment of the surface amounts to 0.01 to 20 eV, preferably 0.5 to 8 eV.

Adhesion of the bacteria or the blood components is prevented if nanoparticles are uniformly distributed on a surface at intervals of 10-3000 nm, preferably 50-1000 nm. The optimal distance is dependent on the size of the particles applied. The microparticles and nanoparticles can be obtained according to different methods, such as, for example, shredding methods, high-pressure homogenization, shredding methods at high speeds of rotation (for example Ultraturrax), ultrasound, or other methods such as emulsification or evaporation methods, emulsion/diffusion methods, or solvent displacement methods. The nanoparticles and microparticles used can—as described in claim 6—be additionally doped with antimicrobially active substances/natural substances, pharmaceutical or cosmetic active substances, masking ingredients, such as tensides or PEG or polylysines, one or more mineral substances, nutrient supplement substances, radical scavengers, vitamins, particularly Vitamin C, or silver particles, also with reactive multi-functional linker molecules (such as glutaraldehyde, toluene-2,4-diisocyanate (TDI), 1-ethyl-3-(3-dimethylaminopropyl) carbodiimide (EDC).

The homogeneous distribution of the nanoparticles and microparticles on the surface can be implemented both using a dipping method and using a spraying method, or also using a spray-drying method. Also, application of the solid nanoparticles and microparticles can be implemented under the effect of plasmas.

In this connection, coatings with lipid nanoparticles are particularly advantageous, since these can be easily produced in large amounts and in sterile manner, and are also well suited as carriers of active substances. However, coatings with suitable biodegradable polymer carriers (for example lactide-glycolide, polyhydroxybutyric acid, or polyorthoester), or chitosans, also chemically modified chitosans, water-soluble or water-insoluble chitosans are possible. Other possibilities consist in that sugar compounds are used as the carrier material (for example cyclodextrin). Substances that have an antimicrobial effect can be worked in as active substances for encapsulation.

By means of adding other masking ingredients, for example surfactants (for example tensides or PEG, polylysines), additional antibacterial and masking or protein-repelling or blood-repelling properties can be generated. By means of targeted modification of the surface charge and hydrophobia, the surface properties can be improved. This can take place, for example, by means of mantling the particles with nonyl phenols (Antarox, Gafac) and/or non-ionic block copolymers (poloxamer, poloxamine). Aside from the significant reduction in hydrophobia, a reduction in the particle charge is also connected with this process. Furthermore, the adhesion of undesirable substances such as blood or proteins is reduced or avoided by means of the method. Contamination of the surface is also prevented by means of the microparticles and nanoparticles that are applied.

According to the invention, a structured arrangement of the microparticles and nanoparticles can be implemented by means of partial treatment of the surface with the plasmas.

By means of controlled formation of covalent bonds and/or hydrogen bridge bonds and/or van der Waals bonds, new functionalities can also be produced on the surface, which are not achieved by the starting material, nor by the microparticles and nanoparticles that are applied, by themselves.

According to the invention, subsequent surface treatment with a suitable non-thermal plasma, which fixes the particles in place on the surface, is extremely advantageous (see exemplary embodiment). In this final method step, germ killing is also combined with an improvement in the coating structure.

This step can be eliminated, however, in the case of a particularly advantageous pretreatment (functional chemical groups on the surface) by means of a plasma, so that only one step is necessary.

The task of disinfection and subsequent covalent bonding or other bonds such as hydrogen bridges or van der Waals bonds of the particles after a layer of nanoparticles and microparticles applied by means of a dipping method or a spraying method or a drying method or under the effect of a plasma is accomplished, according to the invention, in that the surface prepared with particles is exposed to the plasma of a non-thermal discharge at a suitable distance (0.5-200 nm, depending on the plasma method) and for a sufficient amount of time. The conditions are determined by the specifics of the discharge array used. In particular, the type of excitation, the geometry, the process pressure, the geometric placement and dimensions of the reactor, as well as the process gases used, their admixtures and flow velocities play a role here. Another important process parameter is the power fed in. The use of electrode-free arrays, such as microwave discharges or inductively coupled HF plasmas, for example, contaminations caused by electrode material that is worn away are furthermore avoided. When using normal-pressure discharges (for example dielectrically impeded discharge or HF capillary discharge), vacuum apparatuses are eliminated. The arrays according to the invention can serve for treatment and/or coating of inner and outer surfaces, in other words the treatment/coating can also take place in cavities. The adhesion strength of the microparticles and nanoparticles can be influenced in targeted manner by means of setting the plasma conditions. In the exemplary embodiments, it is demonstrated that the surfaces produced by means of the combination method, with optimized posttreatment, are stable with regard to six rinsing procedures. Tests for the re-colonization of bacteria on rinsed surfaces resulted in a significant reduction in recontamination due to microbial growth.

Use of the method, according to the invention, or of the materials produced, is described in claim 13.

According to the invention, the method opens up a number of new applications:

a) Coating of Medical Products and Instruments that can be Conditioned

The method offers the possibility of outfitting medical products and instruments, for example catheters, with a coating that is removed again when the instruments are conditioned by means of suitable washing methods. By means of the coating, the slide properties in the case of catheters, for example, are actually improved as compared with the new products. By means of selecting lipids having a low melting point for the coating with microparticles and nanoparticles, coatings are obtained, according to the invention, that are stable at body temperature, but can be removed again after use, in a chemical disinfection washing method between 50-80° C.

This process of removal, which can be controlled by means of the type of particles and the plasma method that is carried out (particularly the intensity of the plasma providing the posttreatment), clearly distinguishes the method from the methods that have already been established, such as, for example, coating with silver nanoparticles.

In conditioning, it is possible to apply the coating again after cleaning. Permanent deposition of bacteria, pyrogens, and blood components is prevented by means of regular removal and application of the layer. For special instruments such as catheters, this can be very advantageous. Conditioning can advantageously be carried out as follows, using the invention:

- cleaning the used device or the instrument, in this connection removing the coating that was applied during the previous conditioning,
- pretreatment with a non-thermal low-pressure plasma with simultaneous inactivation of all germs and pyrogens that might still be present (presterilization),
- coating with microparticles and nanoparticles under aseptic conditions,
- fixation of the microparticles and nanoparticles in place by means of the effect of a plasma,
- functional inspection under aseptic conditions,
- packaging under aseptic conditions,
- sterilization in the final packaging, using an approved method.

b) Outfitting Surfaces of Switches, Keyboards, Handles of Devices, if Necessary by Way of Protective Films For this use according to the invention, a stronger, more permanent application of the particles is required. Service devices such as the input keyboards of computers, instruments, and switches must frequently be touched by the hands of medical personnel. In this connection, such keyboards can be contaminated with dirt and pathogens. Specifically the keyboards of computers can thereby become the starting point of nosocomial pathogen transfer. Using the method according to the invention, it is possible to outfit the surface with an antimicrobial agent and thus to avoid the transfer of germs. In an advantageous embodiment, the antimicrobial effect is provided by a protective film with which the switches, handles, and other surfaces that must frequently be touched with the hands are covered.

c) Improving Corrosion Protection

Since substances that are derived from the metabolism of the microorganisms can attack the material surface. Protection against biocorrosion is achieved by means of preventing adhesion of microorganisms. Furthermore, chemical corrosion can also be reduced by means of the coating.

d) Coating of Materials Produced on the Basis of Cellulose

The coating method according to the invention is also suitable for textiles and, particularly preferably, for covering materials for wound care. Particular advantages are achieved, according to the invention, by means of the coating. In the case of wound coverings on the basis of polyurethane, adhesion of bacteria is restricted. In this way, wound coverings are obtained with which entrainment of the germs to areas that were not previously infected is prevented. Wound healing can be positively influenced by means of active substances that are worked in. To support wound healing, natural substances and/or pharmaceutical active substances, one or more mineral substances and/or radical scavengers and/or vitamins, quaternary ammonium salts or substances for the stimulation of leukocytes or for activation of the reticulo-endothelial system can be worked into the nanoparticles. Furthermore, biomasses that contain lipids, which can be obtained from algae, cyanobacteria and/or fungi or plant extracts can also be used as a layer material.

The methods a) to d) can be carried out in open systems, since final sterilization after the functional test and packaging is possible using conventional sterilization methods in the case of the products.

If products are required that cannot be sterilized using conventional methods, it is possible to carry out disinfection and coating in a closed system. In this connection, sterile products are achieved.

e) Adhesions

The method is also suitable for connecting components and/or films made of different materials, preferably of plastics, but also natural substances and modified natural substances. Because of different thermal and mechanical properties, such connections are difficult to produce. However, the connections play a role both for medical devices, with simultaneous avoidance of contaminations, and in connection technology for pharmaceutical research, biomedical in vitro diagnostics, and in areas in which harmful side effects of known adhesives or their layer thicknesses greatly restrict their use, such as for foods packaging, for example. The nanoparticles themselves or their fillings, respectively, serve as adhesives in this connection. For this purpose, the surfaces of the materials can be brought into contact before and/or after coating with the nanoparticles, in order to achieve a uniform distribution of the nanoparticles on the surface and reactive bonding locations. The bonding locations react with the nanoparticles or their fillings under the influence of pressure and/or temperature. The nanoparticles can of all the materials already mentioned in the previous section, and can additionally be filled with multifunctional crosslinking reagents (for example di-epoxies, triamines, multi-acids, dialdehydes).

EXEMPLARY EMBODIMENTS

In the following, the invention will be explained in greater detail using preferred exemplary embodiments, making reference to the figures, but without restricting the invention to the examples mentioned.

Example 1

Production of the Lipid Nanoparticles

TABLE 1

Formulation of the nanoparticles and microparticles from the lipid cetyl palmitate

| Substance | Amount in g |
| --- | --- |
| Lipid base | 5.00 |
| Emulsifier (Plantacare 2000 ®) | 0.05 |
| Demineralized water | 45.00 |
| Homogenization cycles | 4 |

The lipid is heated to a temperature of 80° C. Separately from this, an aqueous emulsifier solution is heated to the corresponding temperature (80° C.). Afterwards, the two phases are combined at the desired homogenization temperature. Then the mixture is processed with the aid of an Ultra Turrax T25 from the company Janke and Kunkel GmbH & Co KG (Staufen, Germany), in an emulsification process, at 8000 revolutions per minute and a duration of 30 seconds. The suspension is then homogenized four times with a piston-gap, high-pressure homogenizer Micron Lab 40 (APV-Gaulin, Lübeck), at a pressure of 500 bar and a temperature of 80° C.

Figure 2:
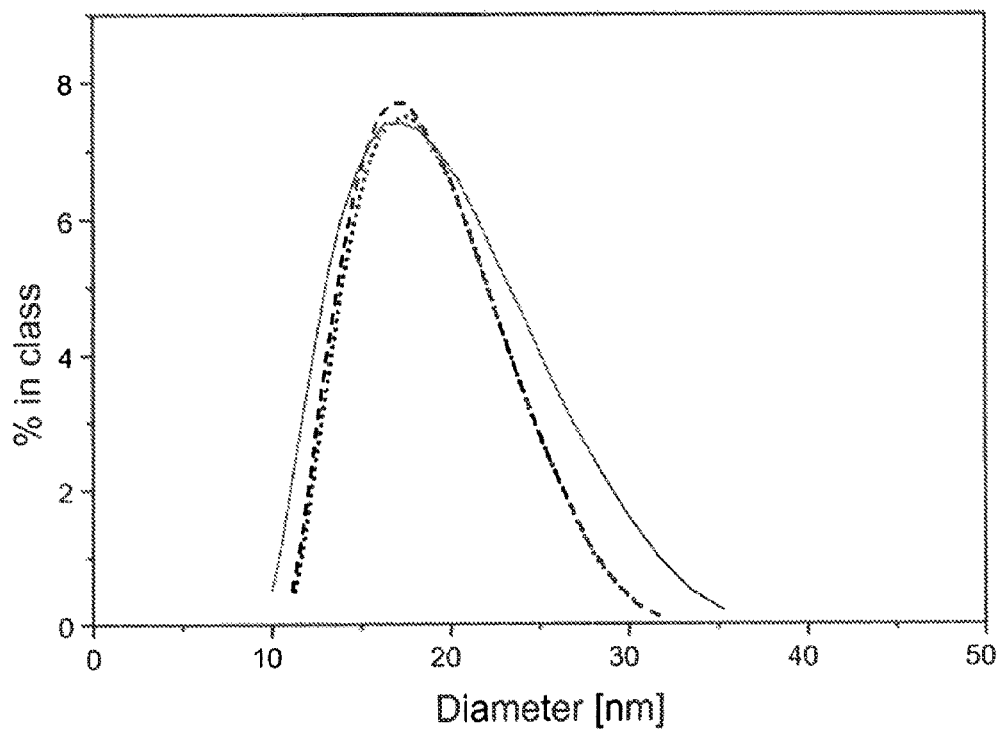
FIG. 2 shows the particle size distribution of cetyl palmitate lipid nanoparticles.

FIG. 2 shows the particle size distribution of cetyl palmitate lipid nanoparticles.

Example 2

Production of the Lipid Nanoparticles Charged with Active Substance

TABLE 1

Formulation of the nanoparticles and microparticles from the lipid cetyl palmitate

| Substance | Amount in g |
|---|---|
| Lipid base | 5.00 |
| Emulsifier (Plantacare 2000 ®) | 0.05 |
| Demineralized water | 44.50 |
| Active substance (Vitamin C) | 0.5 |
| Homogenization cycles | 4 |

The lipid is heated to a temperature of 80° C. The active substance is dispersed in it. Separately from this, an aqueous emulsifier solution is heated to the corresponding temperature (80° C.). Afterwards, the two phases are combined at the desired homogenization temperature. Then the mixture is processed with the aid of an Ultra Turrax T25 from the company Janke and Kunkel GmbH & Co KG (Staufen, Germany), in an emulsification process, at 8000 revolutions per minute and a duration of 30 seconds. The suspension is then homogenized four times with a piston-gap, high-pressure homogenizer Micron Lab 40 (APV-Gaulin, Lübeck), at a pressure of 500 bar and a temperature of 80° C.

Example 3

Production of the Nanoparticles and Microparticles from Lipids for Encapsulation with Prednisolone from Cetyl Palmitate

TABLE 2

Formulation of the lipid nanoparticles and microparticles for encapsulation of active substances (prednisolone)

| Substance | Amount in g |
|---|---|
| Biomass | 5.00 |
| Pluronic F68 | 0.05 |
| Demineralized water | 45.00 |
| Prednisolone | 0.5 |
| Homogenization cycles | 4 |

The prednisolone is worked into the melted lipid mass. Separately from this, an aqueous emulsifier solution is heated to the corresponding temperature (80° C.). Afterwards, the two phases are combined at the desired homogenization temperature. The mixture is processed with the aid of an Ultra Turrax T25 from the company Janke and Kunkel GmbH & Co KG (Staufen, Germany), in an emulsification process, at 8000 revolutions per minute and a duration of 30 seconds. The suspension is then homogenized four times with a piston-gap, high-pressure homogenizer Micron Lab 40 (APV-Gaulin, Lübeck), at a pressure of 500 bar and a temperature of 80° C.

The nanoparticles produced can be used to coat implants.

Example 3 Combination Methods

Studies of the materials showed that plasma pretreatment is required for better distribution of the particles. Pictures taken with the aid of electron microscopy documented that without plasma pretreatment, a very non-uniform distribution of the lipid nanoparticles on the surface was present. In contrast, it was possible to achieve a uniform distribution on the surface with the aid of the plasma pretreatment, at an average electron energy of 1.3 eV.

Figures 3, 4:
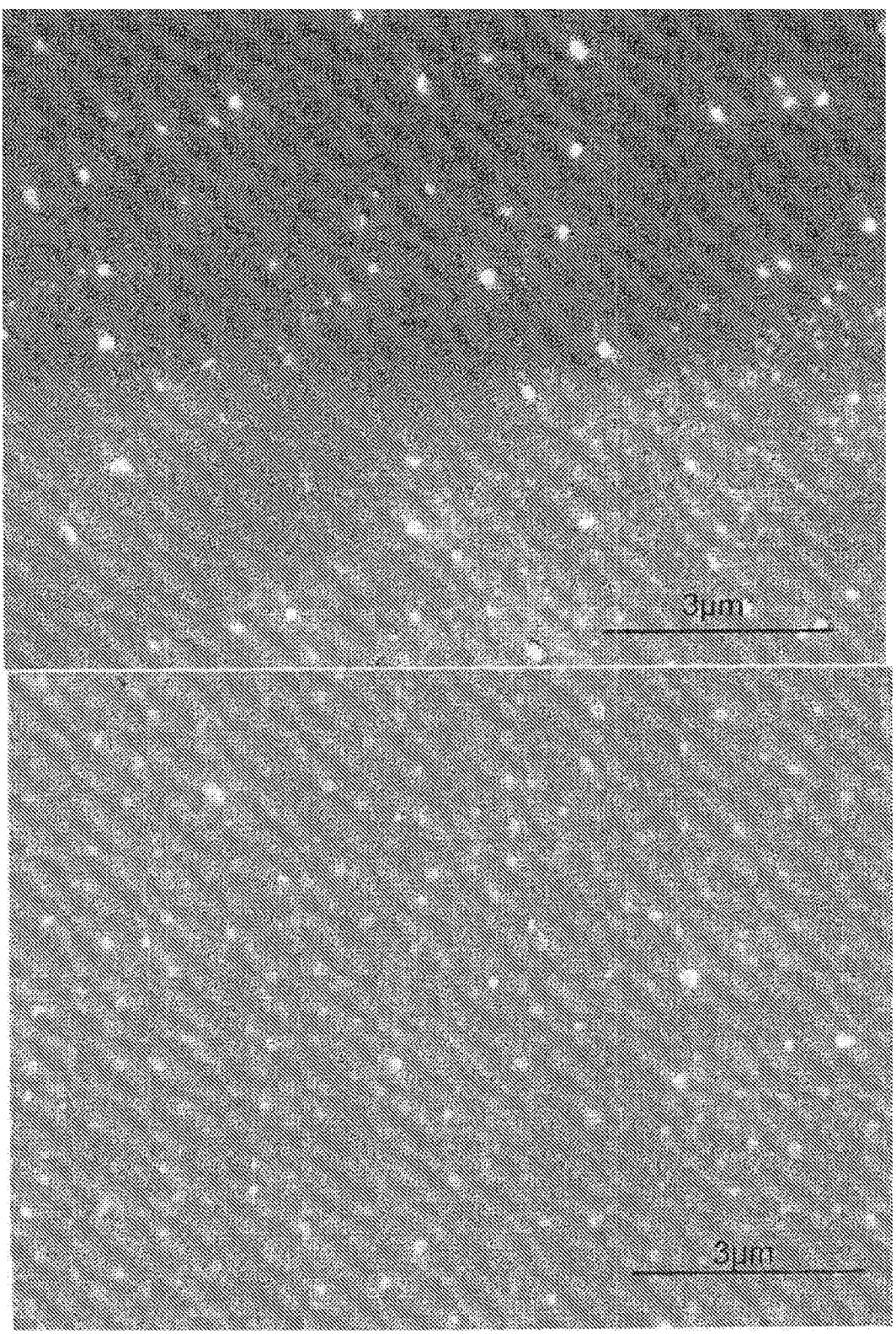
FIG. 3 shows a REM image of PE surfaces without plasma pretreatment.
FIG. 4 shows a REM image of PE surfaces with plasma pretreatment.

FIG. 3 shows an REM image of PE surfaces without plasma pretreatment.

1. The pretreatment took place by means of non-thermal plasma. From the spectrum of the possible plasma sources, the principle was demonstrated using two examples: 1. The medical products were exposed to the plasma of an HF capillary jet over a time period of 350 s [R. Foest, E. Kindel, A. Ohl, M. Stieber, and K.-D. Weltmann, *Plasma Phys. Contr. Fusion* 47 (2005) B525-B536], which was fed with argon and worked at normal pressure conditions in ambient air.

2. It was possible to carry out the pretreatment in a low-pressure microwave plasma with oxygen as the process gas ($O_2$ 0.5 mbar, 200 W, 200 s), whereby the process conditions corresponded to usual treatments [W. Besch, K. Schröder, A. Ohl, *Plasma Process. Polym.* 2005, 2, 97-103].

Both methods led to the same results with regard to the uniform distribution of the lipid nanoparticles and microparticles on the surface.

These improved surface properties had the result that a clearly more uniform distribution of the nanoparticles became possible. Coating with the lipid nanoparticles and microparticles took place by means of dipping the materials. The nanoparticles produced in Example 1 were used for this purpose.

FIG. 4 shows an REM image of PE surfaces with plasma pretreatment.

According to the invention, a plasma posttreatment was carried out in the next method step. For this treatment, the same apparatus as for the pretreatment step described above can be used. In this case, an inert gas, for example argon, can serve as the process gas. The average electron energy was 1.2 eV. In the example plasmas described, an argon plasma was used. The treatment times lie in the time period of 100-200 s. With the aid of this method step, it was possible to covalently bond the nanoparticles to the polymer surface.

Tests Concerning Re-Colonization of Bacteria on the Nanoparticulate Surfaces

For this purpose, the polyethylene carriers were tested for recontamination with microbial growth. First, 0.01 ml bacteria suspension (MRSA North German epidemic strain, $10^6$ germs) was applied to the carriers, which were already coated. Subsequently, the carriers were rinsed three times with 5 ml NaCl solution (pipette) per carrier. The rinse solutions were collected and subsequently applied to an agar plate, in each instance. The agar plates were then incubated at 37° C. for 24 hours. Afterwards, the colonies of the MRSA North German epidemic strain were counted.

TABLE 4

Study concerning recontamination with microbial growth of HDPE carriers with MRSA after three-time rinsing experiment after plasma pretreatment and posttreatment (normal-pressure plasma)

| Sample number/rinsing procedure | Time in seconds | Number of colonies |
|---|---|---|
| PJ01/1 | 130 | 0 |
| PJ01/2 | 130 | 0 |
| PJ01/3 | 130 | 0 |
| PJ02/1 | 190 | 0 |
| PJ02/2 | 190 | 0 |
| PJ02/3 | 190 | 0 |
| PJ03/1 | 260 | 0 |
| PJ03/2 | 260 | 0 |
| PJ03/3 | 260 | 0 |
| K1/1 | 190 | 1048 |
| K1/2 | 190 | 167 |
| K1/3 | 190 | 7 |

TABLE 5

Study concerning recontamination with microbial growth of HDPE carriers with MRSA after six-time rinsing experiment after plasma pretreatment and posttreatment (normal-pressure plasma)

| Sample number/rinsing procedure | Distance from nozzle [relative unit] | Number of colonies |
|---|---|---|
| PJ04/4 | 1 | 102 |
| PJ04/5 | 1 | 81 |
| PJ04/6 | 1 | 15 |
| PJ03/4 | 3 | 229 |
| PJ03/5 | 3 | 183 |
| PJ03/6 | 3 | 99 |
| K1/4 | 2 | 2800 |
| K1/5 | 2 | 380 |
| K1/6 | 2 | 260 |

After rinsing experiments, it was shown that the nanoparticles were bonded so tightly to the surface, under the plasma conditions used, that freedom from germs was present in three rinsing experiments. However, it became clear in renewed rinsing experiments that no adhesion of the nanoparticles was present.

By means of a somewhat modified plasma treatment, it was possible to improve the adhesion of the nanoparticles. This documents freedom from germs after up to six rinsing procedures.

TABLE 6

Study concerning recontamination with microbial growth of HDPE carriers with MRSA after six-time rinsing experiment after plasma pretreatment and posttreatment (normal-pressure plasma)

| Sample number/rinsing procedure | Distance from nozzle [relative unit] | Number of colonies |
|---|---|---|
| PJ06/4 | 2 | 0 |
| PJ06/5 | 2 | 0 |
| PJ06/6 | 2 | 0 |
| K2/4 | 1 | 1740 |
| K2/5 | 1 | 35 |
| K2/6 | 1 | 20 |

Example 5

The polylactide-glycolide particles applied to an HD polyethylene surface are very hydrophilic. PLG particles having a modified monomer composition, particularly copolymers with a high D-lactide or L-lactide content, are increasingly hydrophobic. The cause for this is formed by crystalline regions of the two stereoisomers, which are impermeable for the water. D,L-polylactic acid, as an amorphous substance, on the other hand, promotes water absorption into the matrix.

Under the experimental conditions indicated, the particles are stable. Hydrolytic decomposition begins after 4-6 weeks in the case of the polymer carriers.

By means of TEM, we found an average number-weighted radius of 10 μm for the PLG microparticles. The particles are very polydisperse and also highly porous (FIG. 5).

Figure 5:
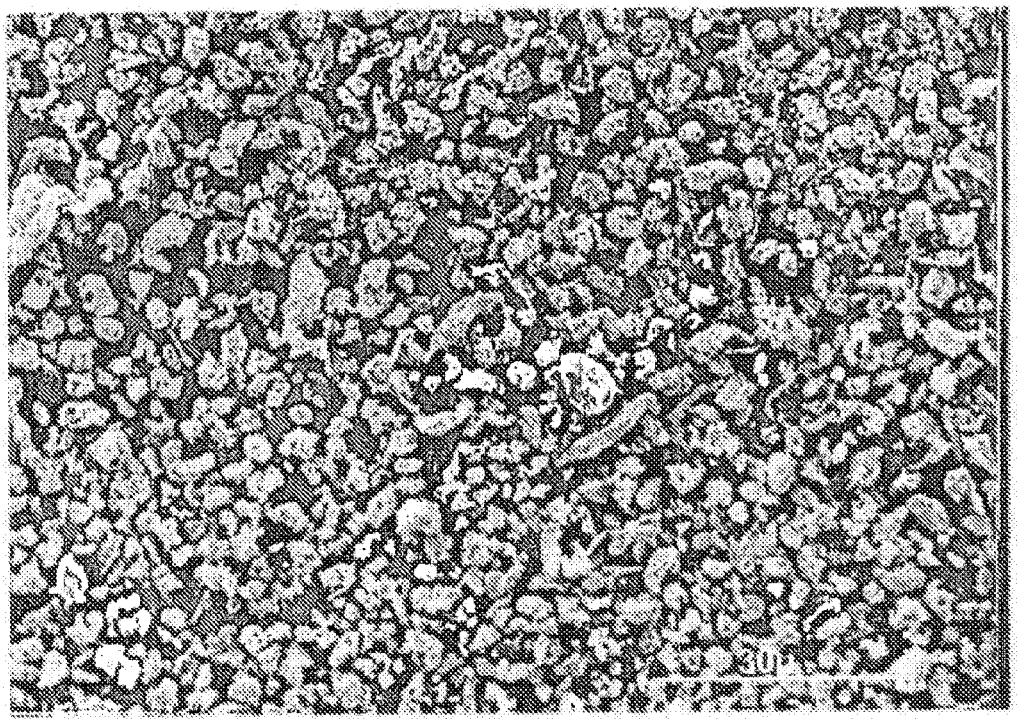
FIG. 5 shows a REM image of the PLG microparticles.

FIG. 5 shows a REM image of the PLG microparticles (preparation: ultrasound atomization).

Because of the high particle density (769.1 mg·cm$^{-3}$), however, only an average particle-specific total surface is available, at a constant weigh-in (19.1 g).

Example 6

Nanoparticles charged with different active substances by means of plasma coating methods were applied to HDPE surfaces. The rinsing experiments show the advantageous properties of the coatings of nanoparticles charged with active substance.

Figure 6:
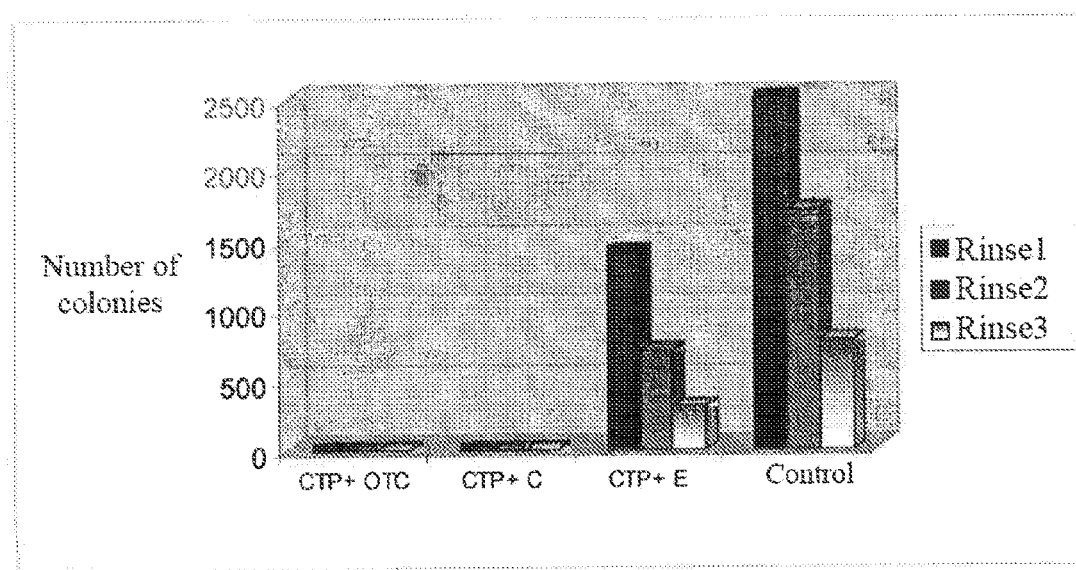
FIG. 6 shows the plasma pretreatment, coating, and plasma posttreatment carrier: PE/hard test for germ reduction after simple recontamination with microbial growth ($10^6$).

FIG. 6 describes the plasma pretreatment, coating, and plasma posttreatment carrier: PE/hard test for germ reduction after simple recontamination with microbial growth ($10^6$).

Example 7

The release of prednisolone from cholesterol nanoparticles lasts for about three weeks and stops at approximately 95% of the actual active substance content. The active substance is liberated from the particles almost completely.

Figure 7:
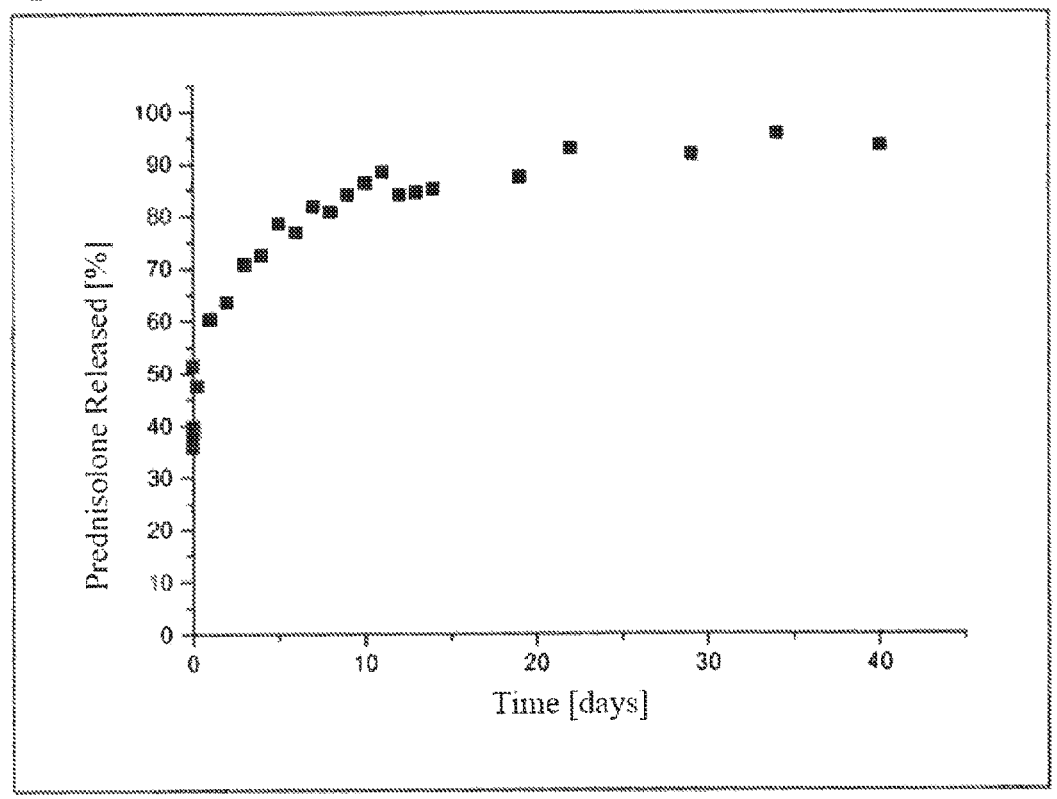
FIG. 7 shows the time progression of the active substance release from 2% prednisolone/cholesterol nanoparticles with reference to the actual content.

FIG. 7 shows the time progression of the active substance release from 2% prednisolone/cholesterol nanoparticles with reference to the actual content; N=2).

Example 8

The zeta potential of the nanoparticles coated with poloxamer 407, poloxamine 908, and Antarox CO 990 was reduced with the increase in the coating layer. The charge reduction effect could not be utilized in the adsorption with Gafac RE 960. The tenside carries a charge at the end of the EO chain. The charge is located at the outer surface of the coated nanoparticles. This new surface charge is superimposed on the charge reduction effect of the coating. The zeta potentials obtained for Gafac RE 960 therefore lie in the vicinity of the potentials of the non-coated nanoparticles.

TABLE 7

Zeta potentials of the polymer particles, coated with four different tensides (poloxamine 908, poloxamer 407, Antarox CO990, Gafac RE960) in NaCl solution (50 μS)

| Coating material | PLGA |
|---|---|
| without | −37.5 |
| Poloxamine 908 | −2.5 |
| Poloxamer 407 | −0.8 |
| Antarox CO 990 | −7.9 |
| Gafac RE 960 | −26.5 |

Example 9

Figure 8:
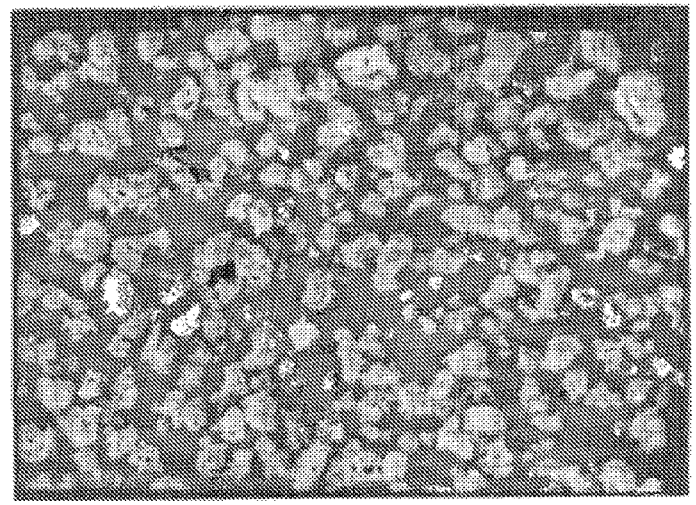
FIG. 8 shows a REM image of the GMA-10% microparticles.

FIG. 8 shows a REM image of the GMA-10% microparticles (preparation: ultrasound atomization).

The surface properties of the glycol methacrylate (GMA) particles vary on the basis of the changes in the monomer composition. With an increase in the GMA content, additional functional groups are inserted into the polymer structure. Since the increasing hydrophilia with a reduced adsorption tendency also has an effect on the adsorption of biopolymer components on the medication carrier adsorbate.

Example 10

Two plastic films made of polyethylene and polyether ether ketone are connected with one another. First, the two surfaces are pretreated in air, with normal-pressure plasmas. This brings about activation of the surfaces. Subsequently, the materials are dipped in lipid nanoparticles. Afterwards, the polyether ether ketone is treated with a normal-pressure plasma in nitrogen, the polyethylene is treated in a normal-pressure plasma in oxygen, and they are immediately pressed together at 1 $MN/m^2$ at 45° C. As a result, these materials are connected with an adhesive layer thickness of 200 nm.

Example 11

The plasma activation of polypropylene (PP) took place in a low-pressure microwave reactor with oxygen as the process gas oxygen 0.5 mbar, 200 W, 200 s at an electron temperature of 1.3 eV on polypropylene (PP). The substrate temperature remains below the $T_g$ (glass temperature) of PP, at 40° C., whereby the process conditions corresponded to usual treatments (see Example 3). As a result, a clearly uniform distribution of the nanoparticles, disposed in patterns (see FIG. 8) was possible. The subsequent fixation of the nanoparticles the same apparatus as described above was used. However, argon was used as the process gas at 0.5 mbar, 150 W, 100 s at an electron temperature of 1.2 eV.

In the case of polyether ether ketone (PEEK), the conditions were varied as follows: oxygen 0.5 mbar, 350 W, 300 s, at an electron temperature of 1.4 eV substrate temperature of 65° C.

Example 12

Physical/Chemical Studies of the Coated Surfaces

In order to better understand the process of bonding of the nanoparticles, XPS studies of the coated samples were carried out. The plasma activation took place in a non-thermal plasma (plasma jet) with argon as the process gas. As a result, structured distribution of the nanoparticles (see FIG. 8) in patterns was possible. The measurements were carried out with an X-ray photoelectron spectrometer (XPS), also called ESCA (electron spectroscopy for chemical analysis). The device was an Axis Ultra, Kratos, Manchester, GB.

Figure 9:
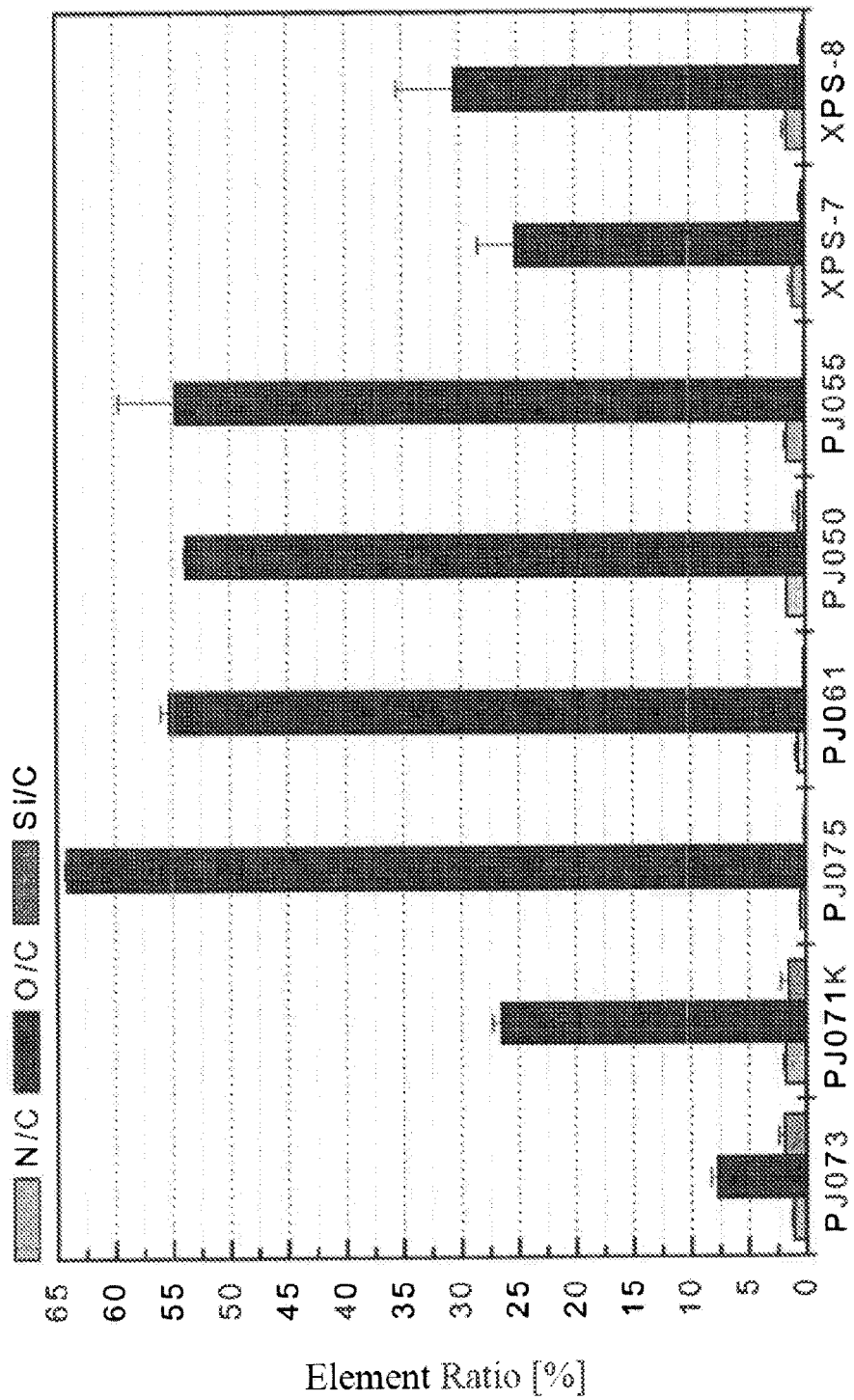
FIG. 9 shows the element ratios of the various samples.

FIG. 9 shows the element ratios of the various samples.

For this purpose, uncoated (PJ073), plasma-pretreated (PJ071), coated (PJ075), and posttreated (PJ061, PJ050, PJ055, XPS-7, XPS-8) samples were studied. In FIG. 9, the element ratios N/C, O/C, and Si/C can be seen. The N/C and Si/C ratios remain almost constant, independent of the plasma treatment, and are only slightly reduced by the nanoparticle layer. The change in the O/C ratio after coating the plastic with nanoparticles (PJ075) should be particularly emphasized. After the plasma treatment, the O/C ratio is slightly and systematically reduced due to the fixation of the nanoparticles.

Figure 10:
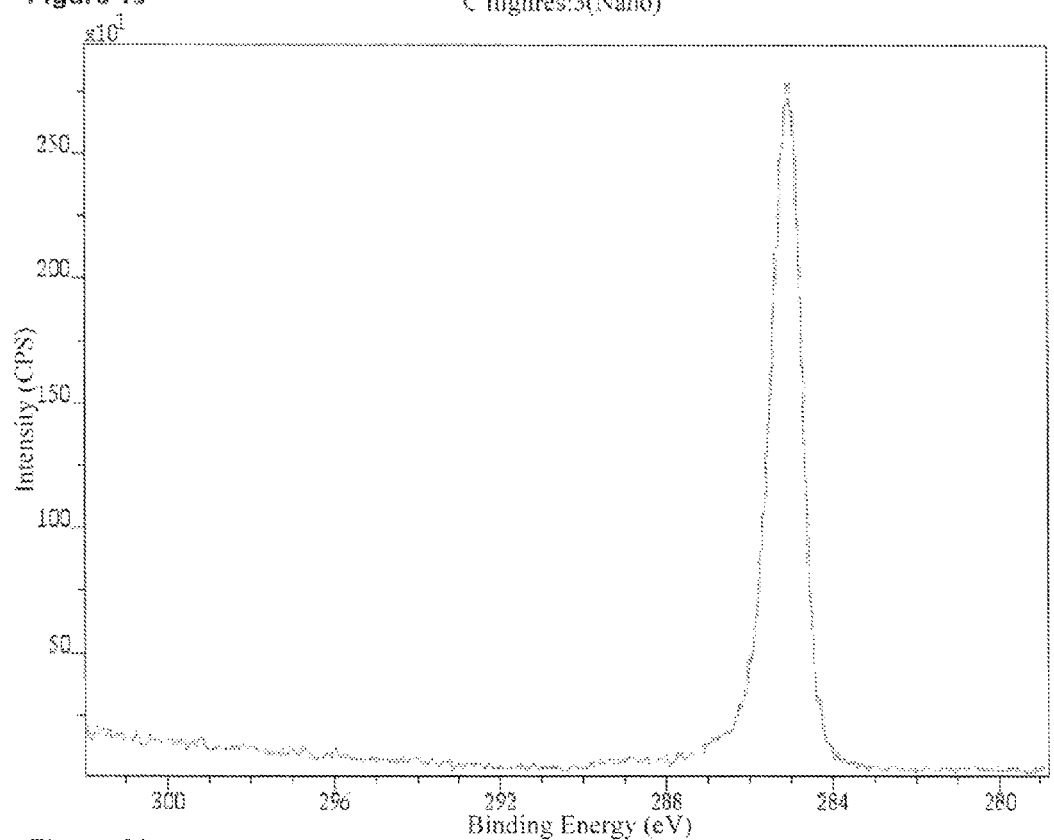
FIG. 10 shows the XPS spectrum of a sample.

FIG. 10 shows PJ703: PE/hard, disinfected, without pretreatment, uncoated.

Figure 11:
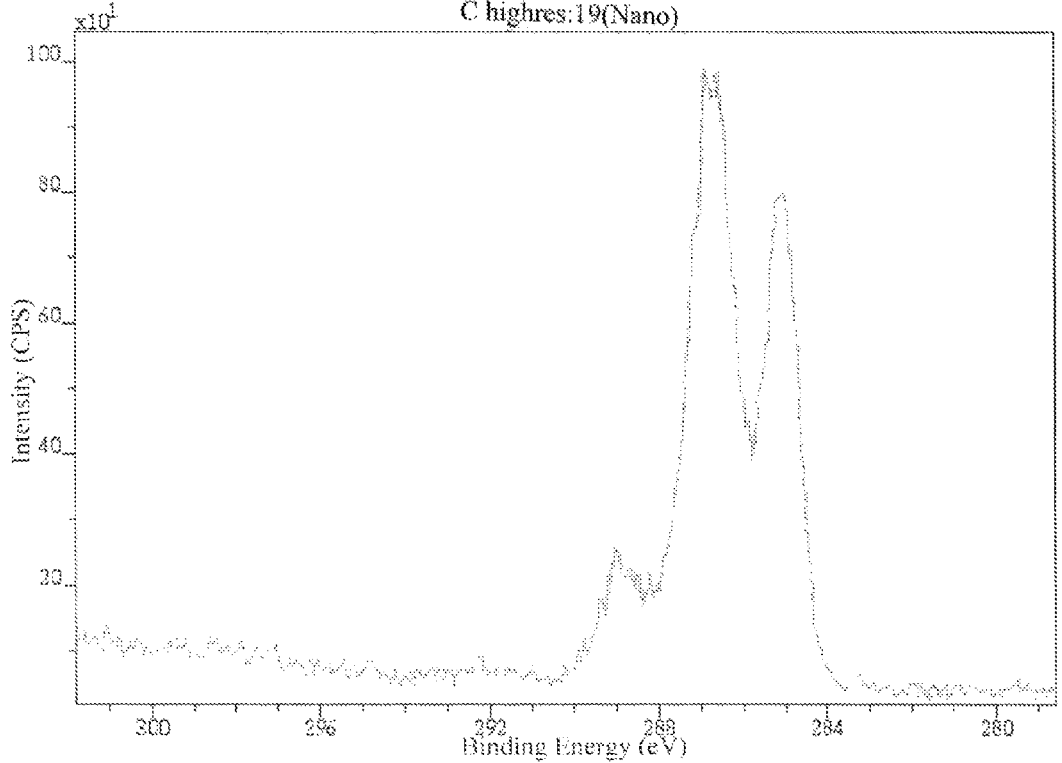
FIG. 11 shows the XPS spectrum of a sample.

FIG. 11 shows PJ050: C 1s peak PE/hard; pretreatment: 40 W, 20 sccm argon; posttreatment: 30 W; 20 sccm argon.

The analysis of the C1s peak of the plasma-treated sample shows a clear influence as the result of the plasma treatment. The pure substrate PE contains only C—C and C—H bonds at 285 eV. After the treatment, the C1s demonstrates the bonds C—H, C—C aliphatic (like PE), C—NH, C—O, C═O, and COO. The substrate temperature, at 40°, lies below the glass transition temperature of polyethylene, whereby the process conditions corresponded to usual treatments (see Example 3). As a result, a clearly uniform coating was possible. If the plasma treatment is too long and thus the substrate temperature is too high (70° C.), destruction of the particles comes about (reduction of the peak at 286, 7 eV), which is typical for coating with nanoparticles.

Figure 12:
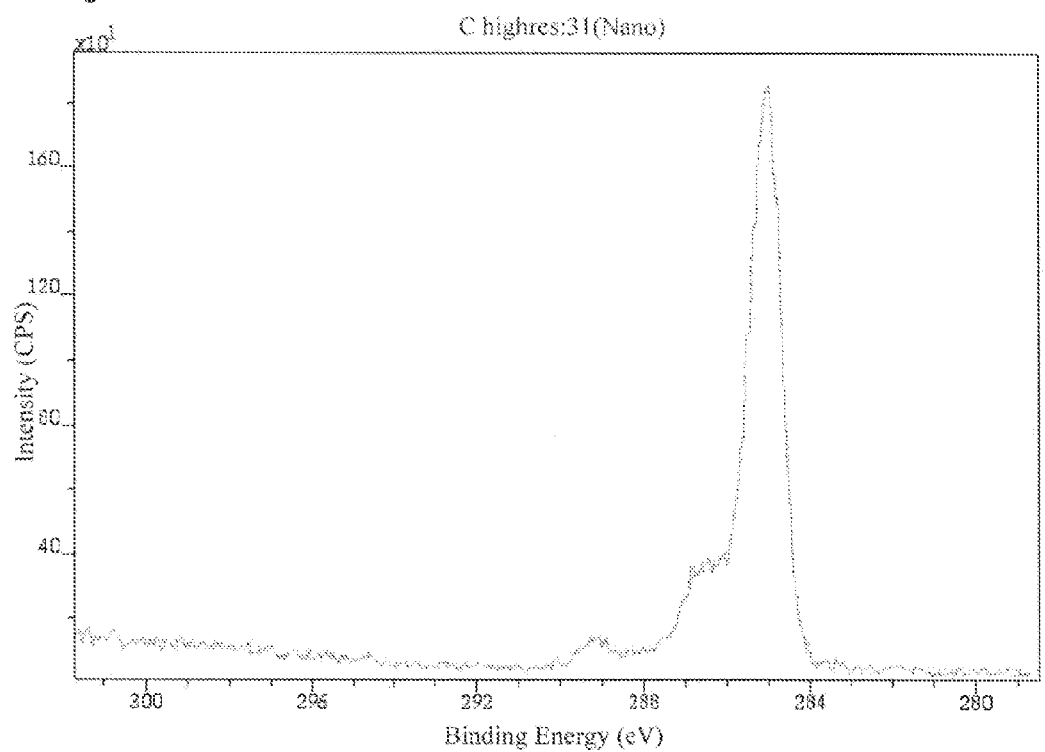
FIG. 12 shows the XPS spectrum of a sample.

FIG. 12 shows the XPS-7 pretreatment: 40 W, 20 sccm argon; posttreatment: 50 W; 20 sccm argon. Very similar to the uncoated and pretreated sample.

An overly high electron energy in the posttreatment also proved to be negative; it was also made clear in a reduction of the peak at 286, 7 eV. The results of the XPS studies correlate very well with the results of the rinsing experiments concerning bonding of the nanoparticles to the surface and their antibacterial properties of the coating.

Example 13

Methods

Uncoated PE strips are contaminated with 100 μl freshly obtained blood that contains HBV-DNA (obtained from patients with HBe-positive virus Hepatitis B). For simulation of mechanical cleaning, the PE strips were wiped off with swabs. The swabs were eluted in 3 ml buffer solution. Detection of HBV-DNA was carried out in the rinsing water as described by Jülich & von Woedtke (Reprocessing of thermosensitive materials—efficacy against bacterial spores and viruses. J. Hosp. Infection. 47 (2001): 1-11). Test kits from Abbott-GmbH Wiesbaden were used. In order to ensure that no viruses are located on the instruments from which the blood residues were removed completely, all the instruments were treated a second time using the recovery method. In a second experiment, the PE strips were placed into a 2% glutaraldehyde solution after the blood was allowed to dry on, and processed further as described above, after the glutaraldehyde was rinsed off.

Parallel to this, the PE strips were coated according to the invention. The contamination took place as with the controls, with 100 µl of the Habe-positive serum. The coating was removed at 80° C., by means of shaking with an instrument cleaner (Bode Chemie company) on the vortex shaker. After drying, the PE strips were coated again with lipid nanoparticles, according to the invention. Afterwards, the PE strips are wiped off with swabs. The swabs were eluted with 3 ml buffer solution. In the rinsing water, the detection of HBV-DNA was carried out as for the controls. Here again, in a second experiment, disinfection with glutaraldehyde took place as described above.

Results

It is possible to detect HBV-DNS reliably on the instruments (Table 8). This contamination cannot be removed by means of disinfection with glutaraldehyde. Possibly, the contamination is actually fixed in place, so that cleaning by means of disinfectants that produce fixation is actually made more difficult (Table 9). The results correspond to information in the literature, according to which instruments contaminated with duck hepatitis virus remain infectious even after being placed in glutaraldehyde solution, and are transferred, with great likelihood, in a subsequent operation.

In the case of the instruments coated and conditioned according to the invention, the HBV-DNA detection remained below the detection limit (<15 copies/ml; Tables 8 and 9).

Example 14

Methods

Uncoated PE strips were contaminated with 100 µl freshly obtained blood that contains HBV-DNA (obtained from a patient with HBe-positive virus Hepatitis B). In the case of three samples, the contamination is determined using a swab sample (see above).

In the case of three other samples, for simulation of mechanical cleaning, 3 ml instrument cleaner (Bode-Chemie company) was poured over the PE strips, and they were brushed off with a Cytobrush. Afterwards, a smear was obtained using the swab method, and detection of HBV-DNA was carried out as described by Jülich & von Woedtke (Reprocessing of thermosensitive materials—efficacy against bacterial spores and viruses. J. Hosp. Infection. 47 (2001): 1-11).

Parallel to this, the PE strips were coated with nanoparticles, according to the invention, according to Example. The contamination took place as with the controls, with 100 µl of the HBe-positive serum. The coating was removed at 80° C., by means of shaking with an instrument cleaner (Bode Chemie company) on the vortex shaker. Afterwards, the PE strips were brushed off using the Cytobrush, as described above. After drying, the PE strips were coated again with lipid nanoparticles, according to the invention. Afterwards, the sampling with the swab method and the detection of HBV-DNA took place.

Results

In this experiment, as well, it is possible to detect HBV-DNA reliably on the instruments. By means of the mechanical cleaning, the virus contamination is reduced, but virus safety is not achieved (Table 10).

TABLE 8

Detection of contamination with HBV-DNA on instruments without disinfection

| | | Copies × 1000/ml eluate | | |
| --- | --- | --- | --- | --- |
| | | Swab 1 | Swab 1 | Swab 1 |
| Uncoated PE strips | 1st recovery | 573 | 584 | 275 |
| | 2nd recovery | 63 | 80 | 73 |
| PE strips coated and conditioned according to the invention | 1st recovery | no detection of HBV-DNA | no detection of HBV-DNA | no detection of HBV-DNA |
| | 2nd recovery | no detection of HBV-DNA | no detection of HBV-DNA | no detection of HBV-DNA |

TABLE 9

Detection of contamination with HBV-DNA on instruments after disinfection with glutaraldehyde

| | | Copies × 1000/ml eluate | | |
| --- | --- | --- | --- | --- |
| | | Swab 1 | Swab 1 | Swab 1 |
| Uncoated PE strips | 1st recovery | 560 | 783 | 636 |
| | 2nd recovery | 79 | 348 | 781 |
| PE strips coated and conditioned according to the invention | 1st recovery | no detection of HBV-DNA | no detection of HBV-DNA | no detection of HBV-DNA |
| | 2nd recovery | no detection of HBV-DNA | no detection of HBV-DNA | no detection of HBV-DNA |

In the case of the instruments coated and conditioned according to the invention, the HBV-DNA detection remained below the detection limit (<15 copies/ml; Table 10).

TABLE 10

Detection of contamination with HBV-DNA on instruments without disinfection

| | | Copies × 1000/ml eluate | | |
|---|---|---|---|---|
| | | Sample 1 | Sample 2 | Sample 3 |
| Uncoated PE strips | Before cleaning | 920 | 783 | 663 |
| | After cleaning | 107 | 142 | 70 |
| PE strips coated and conditioned according to the invention | After application of the lipid nanoparticles | no detection of HBV-DNA | no detection of HBV-DNA | no detection of HBV-DNA |

Example 15

Transfer of the Coating Method of PE Sample Bodies to Treatment on a Catheter

The positive results of the coating method of PE sample bodies should also be transferred to medical products. For this purpose, angiography catheters and electrophysiology catheters were coated.

By means of optimizing the displacement speed of the plasma jet (4 mm/s) and using a double plasma jet with outer electrodes, it was possible to implement optimal pretreatment and also to guarantee good coupling with the aid of the plasma posttreatment. Testing of the antibacterial effect of the coating on the catheters was carried out as follows:
1. Dividing the catheter into 5 sections (5 cm per section)
2. Contaminating the sections with approximately $10^6$ germs/cm
2. Drying under the laminar box for approximately 3.5 h
2. Microbiological evaluation of the individual sections From the results concerning recontamination with microbial growth of the optimally coated angiography catheters and electrophysiology catheters, it is evident that the MRSA cannot reproduce on the surface of the catheters. In this way, it was possible to guarantee the goal of reducing multi-resistant pathogens in the case of medical products and, at the same time, achieving protection of the medical products from antimicrobial recontamination.

TABLE 11

Tests concerning recontamination of angiography (angio) and EP catheters coated with nanoparticles

| Cath. No., Sample No./Rinsing procedure | Colonies counted |
|---|---|
| Angio1/K190 A/ | |
| 1 | 0 |
| 2 | 0 |
| 3 | 0 |
| Angio1/K191 A/ | |
| 1 | 0 |
| 2 | 0 |
| 3 | 0 |
| Angio1/K192 A/ | |
| 1 | 0 |
| 2 | 0 |
| 3 | 0 |

TABLE 11-continued

Tests concerning recontamination of angiography (angio) and EP catheters coated with nanoparticles

| Cath. No., Sample No./Rinsing procedure | Colonies counted |
|---|---|
| Angio1/K194 Control | |
| 1 | 1053 |
| 2 | 572 |
| 3 | 12 |
| EP1/K195 A/ | |
| 1 | 0 |
| 2 | 0 |
| 3 | 0 |
| EP1/K196 A/ | |
| 1 | 0 |
| 2 | 19 |
| 3 | 2 |
| EP1/K197 A/ | |
| 1 | 0 |
| 2 | 0 |
| 3 | 0 |
| EP1/K198 A/ | |
| 1 | 0 |
| 2 | 0 |
| 3 | 0 |
| EP1/K199 Control | |
| 1 | 1600 |
| 2 | 364 |
| 3 | 33 |

For characterization of the catheters, AFM images of untreated, plasma-treated, and coated surfaces were made. The comparison of the untreated surface with the plasma-treated but uncoated surface shows no marked change in morphology. The roughness increased to a very slight extent, so that no material damage resulting from the plasma jet was visible.

Figure 13:
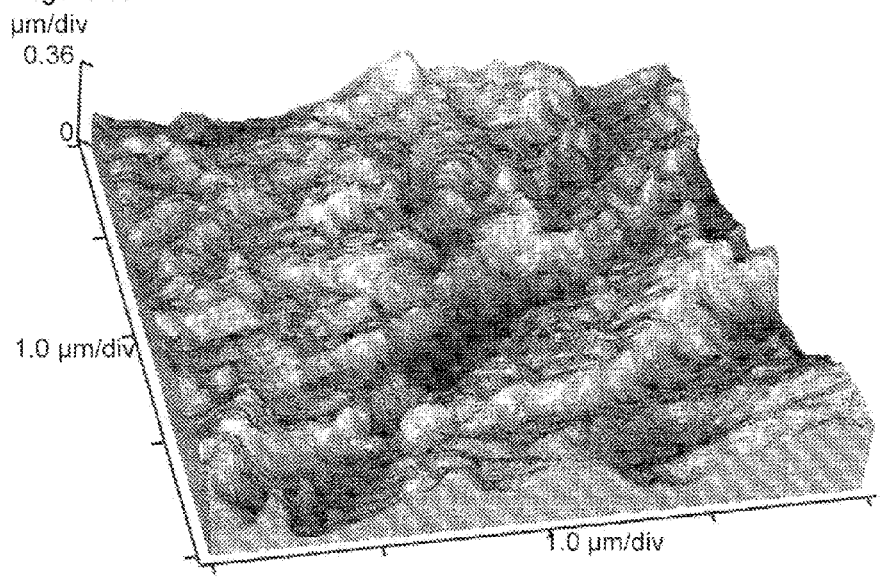
FIG. 13 shows the AFM image of untreated surface.
Figure 14:
FIG. 14 shows the AFM image of plasma-treated but uncoated surface.

FIGS. 13 and 14 show AFM images of untreated and plasma-treated, uncoated surfaces.

The changes resulting from the deposition of lipid particles were very marked and corresponded to the assumptions we postulated. Growth of pathogens is effectively prevented by the regular peak structure.

Figure 15:
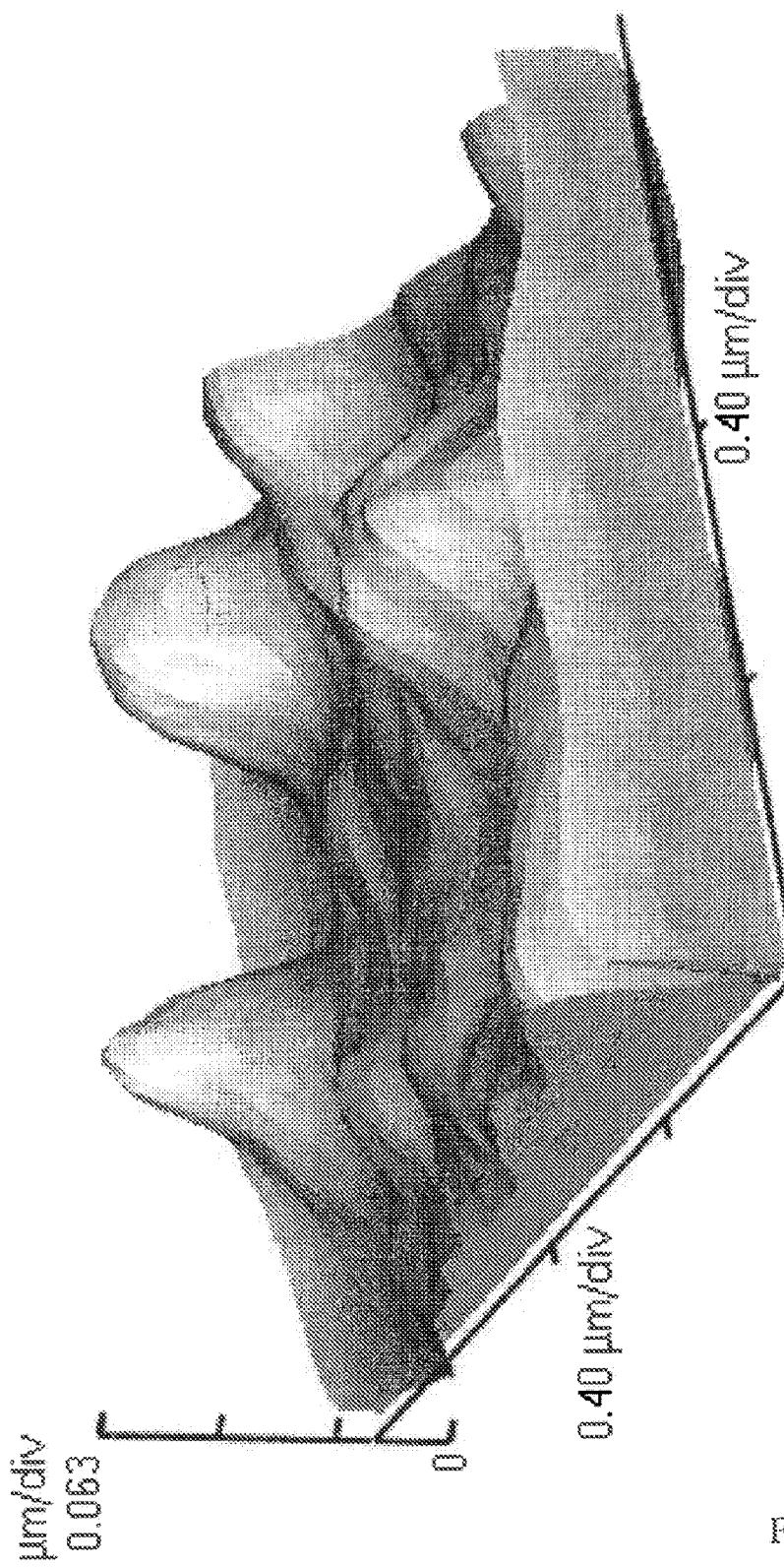
FIG. 15 shows the AFM image of plasma-treated and coated surface.

FIG. 15 shows AFM images of plasma-treated, coated surfaces.

The invention claimed is:

1. A method for coating a polymer surface with microparticles and nanoparticles, comprising:
   a) pretreatment of the polymer surface using a plasma method, wherein the average electron energy of the anisothermal plasma for pretreatment of the polymer surface is from 0.01 to 20 eV,
   b) subsequent application of the microparticles and nanoparticles to the polymer surface,
   c) subsequent fixation of the microparticles and nanoparticles on the polymer surface by a plasma method, wherein an average electron energy of the anisothermal plasma for bonding of the microparticles and nanoparticles to the polymer surface is in the range of 0.01 to 10 eV,
   wherein
   1) the microparticles and nanoparticles are chemically bonded to the polymer surface,
   2) the bonding of the microparticles and nanoparticles takes place with the aid of said anisothermal plasma, for bonding of the microparticles and nanoparticles to the polymer surface, wherein the average electron energy of said anisothermal plasma for bonding lies in the range of the bond dissociation energy of the microparticles and nanoparticles, and thereby the strength of the chemical bond between the polymer surface and the microparticles and nanoparticles are adjusted in variable manner;
   3) the microparticles and nanoparticles are selected from the group of materials consisting of
   lipids
   polymers,
   chitosans, chemically modified chitosans, water-soluble or water-insoluble chitosans,
   dextrins or sugar compounds, and
   biomasses comprising lipids, obtained from algae, cyanobacteria and/or fungi; and
   4) the microparticles and nanoparticles have an average diameter of 10 nm-10 µm, and are distributed on the polymer surface at intervals of 10-3000 nm, structured as a function of the size of the particles applied.

2. The method according to claim 1, wherein the microparticles and nanoparticles are obtained by a method selected from the group of methods consisting of shredding methods, high-pressure homogenization, shredding methods at high speeds of rotation, emulsification or evaporation methods, emulsion/diffusion methods, and solvent displacement methods.

3. The method according to claim 1, wherein the microparticles and nanoparticles are additionally doped with at least one substance selected from the group consisting of
   a) antimicrobially active substances/natural substances,
   b) pharmaceutical or cosmetic active substances,
   c) masking ingredients,
   d) mineral substances,
   e) radical scavengers,
   f) vitamins,
   g) silver particles,
   h) biomasses that contain lipids, and
   i) reactive multi-functional linker molecules.

4. The method according to claim 1, wherein coating with microparticles and nanoparticles takes place by a dipping method or a spraying method or a drying method.

5. The method according to claim 1, wherein the microparticles and nanoparticles are mantled with nonyl phenols and/or non-ionic block copolymers.

6. The method according to claim 1, wherein the coating comprises said lipid and said coating is stable at body temperature, and the lipid is removed again in a chemical disinfection washing method between 50-80° C.

7. The method according to claim 6, wherein the lipid is fixed in place on the polymer surface, after conversion to microparticles and nanoparticles.

8. A process comprising the method according to claim 1, wherein the process is one selected from the group consisting of
   a) germ reduction or disinfection of polymer surfaces,
   b) immobilization of microparticles and nanoparticles on polymer surfaces,
   c) protection of polymer surfaces from re-growth of microorganisms,
   d) production of pharmaceutical or medical products,
   e) transplantation medicine,
   f) conditioning of medical instruments and devices,
   g) an antibiotic carrier, and/or
   h) permanent antimicrobial outfitting of service devices,
   i) improving corrosion protection,
   j) surface modification of implants or in slow-release systems for promoting in-growth as well as preventing implant-associated infections, and/or
   k) for reducing the slide friction or for improving the sliding properties,
   l) accelerating cell growth or for stimulation of leukocytes or for activation of the reticulo-endothelial system,
   m) impregnation of textile materials and/or materials produced on the basis of cellulose, or as cover materials for wound care,
   n) metered release of antimicrobially active substances,
   o) metered release of immune-stimulating active substances,
   p) production of drug delivery systems,
   q) controlled removal of the microparticles and nanoparticles from the polymer surface, and
   r) connecting different materials made from plastics, natural substances, and modified natural substances with adhesive layer thicknesses from 50 to 5000 nm.

* * * * *